United States Patent [19]

Ono et al.

[11] Patent Number: 5,763,231
[45] Date of Patent: Jun. 9, 1998

[54] PROCESS FOR PRODUCING L-LEUCINE

[75] Inventors: Yukiko Ono; Katsuaki Sato, both of Kawasaki, Japan

[73] Assignee: Ajinomoto Co., Inc., Tokyo, Japan

[21] Appl. No.: 610,874

[22] Filed: Mar. 5, 1996

[30] Foreign Application Priority Data

Mar. 30, 1995 [JP] Japan .................... 7-072937

[51] Int. Cl.$^6$ .................... C12P 13/04; C12P 13/06
[52] U.S. Cl. .................... 435/116; 435/106; 435/843; 435/848; 435/849
[58] Field of Search .................... 435/116, 849, 435/106, 843, 243, 848

[56] References Cited

U.S. PATENT DOCUMENTS 3,668,073  6/1972  Kurihara et al. .................... 435/116
3,865,690  2/1975  Okumura et al. .................... 435/116
5,164,307  11/1992  Yoshihara et al. .................... 435/106

*Primary Examiner*—Leon B. Lankford, Jr.
*Assistant Examiner*—Christopher R. Tate
*Attorney, Agent, or Firm*—Oblon, Spivak, McClelland, Maier & Neustadt, P.C.

[57] ABSTRACT

A process for producing L-leucine, which includes incubating an L-leucine-productive microorganism belonging to the genus Corynebacterium, Escherichia, Brevibacterium, or Microbacterium in a culture medium and reacting the resulting cells with saccharides and acetic acid or its salt to form and accumulate L-leucine in the reaction solution. The process improves the amount of L-leucine accumulated and decreases formation of amino acid byproducts.

23 Claims, No Drawings

PROCESS FOR PRODUCING L-LEUCINE

BACKGROUND OF THE INVENTION

1. Field of the Invention

The present invention relates to a process for producing L-leucine. L-leucine is widely used in fields such as medications, food, feed additives and the like.

2. Description of the Prior Art

Known examples of methods of producing L-leucine through fermentation include a method in which a strain of the genus Brevibacterium or Corynebacterium is cultured which requires one or more of isoleucine, threonine and methionine for growth and which is resistant to feedback inhibition or (and) repression by L-leucine [Japanese Laid-Open Patent Application (Kokai) No. 123,877/1975] and a method in which a microorganism of the genus Escherichia coli is cultured which is resistant to β-thienylalanine [Japanese Laid-Open Patent Application (Kokai) No. 72.695/1981].

However, these methods involve problems such that the amount of L-leucine accumulated is not sufficient and amino acids such as L-valine and the like are formed as byproducts.

SUMMARY OF THE INVENTION

One object of the present invention is to provide a process for producing L-leucine using microorganisms, in which L-leucine is produced in industrially acceptable fashion at low cost by improving the amount of L-leucine accumulated and decreasing formation of amino acid by-products.

DESCRIPTION OF THE PREFERRED EMBODIMENTS

The present inventors have found that when a known L-leucine-productive strain is incubated in a culture medium containing, e.g., saccharides as a carbon source and the resulting cells are reacted with one or more saccharides and acetic acid or its salt, formation of L-valine as a by-product is decreased and the amount of L-leucine accumulated is remarkably increased as compared to the reaction with saccharides alone. This finding has led to the completion of the present invention.

That is, the present invention provides a process for producing L-leucine which comprises incubating an L-leucine-productive microorganism belonging to the genus Corynebacterium or Escherichia in a culture medium containing saccharides as a main carbon source, reacting the resulting strain with saccharides and acetic acid or its salt to form and accumulate L-leucine in the reaction solution, optionally collecting the same and optionally purifying the same.

The microorganism used in the present invention may be one or more microorganisms which belong to the genus Corynebacterium or Escherichia and which has L-leucine productivity. The microorganism may be a wild strain, a mutant or a recombinant strain induced through cell fusion or gene manipulation.

The microorganisms of the genus Corynebacterium referred to in the present invention are a group of microorganisms defined in Bergey's Manual of Determinative Bacteriology, 8th ed., p. 599 (1974), incorporated herein by reference, and are bacilli which are aerobic, gram-positive, non-acidophilic and free from sporulation. These were once classified into the genus Brevibacterium but now belongs to the genus Corynebacterium which also include bacteria of the genus Brevibacterium [Int. J. Syst. Bacteriol., 41,255 (1981) incorporated herein by reference]. Thus, the microorganisms of the genus Corynebacterium include bacteria of the genus Brevibacterium and bacteria of the genus Microbacterium which are very close to bacteria of the genus Corynebacterium. Of these bacteria of the genus Corynebacterium, L-leucine-productive strains induced from bacteria which are known as L-glutamic acid-productive bacteria mentioned below are most preferable in the present invention.

*Corynebacterium acetoacidophilum*
*Corynebacterium acetoglutamicum*
*Corynebacterium glutamicum*
*Corynebacterium lilium* (*Corynebacterium glutamicum*)
*Corynebacterium melassecola*
*Brevibacterium divaricatum* (*Corynebacterium glutamicum*)
*Brevibacterium lactofermentum* (*Corynebacterium glutamicum*)
*Brevibacterium saccharolyticum*
*Brevibacterium flabum* (*Corynebacterium glutamicum*)
*Microbacterium ammoniaphilum*

Specific examples of L-leucine-productive strains useful herein are Brevibacterium lactofermentum AJ3718 (FERM P-2516; resistance to 2-thiazolealanine and β-hydroxyleucine and requirement of isoleucine and methionine), Corynebacterium glutamicum AJ3453 (deposited under the terms of the Budapest Treaty at the National Institute of Bioscience and Human Technology, Agency of Industrial Science and Technology, Ministry of International Trade and Industry, 1-3, higashi 1-chome, Tsukuba-shi, Ibaraki-ken 305, Japan, under the accession number FERM BP-5360; resistance to 2-thiazolealanine and B-hydroxyleucine and requirement of isoleucine), and Escherichia coli AJ11478 (deposited under the terms of the Budapest Treaty at the National Institute of Bioscience and Human Technology, Agency of Industrial Science and Technology, Ministry of International Trade and Industry, 1-3, higashi 1-chome, Tsukuba-shi, Ibaraki-ken 305, Japan, under the accession number FERM BP-5361; resistance to β-2-thienylalanine and β-hydroxyleucine).

As a culture medium in which to incubate the above-mentioned microorganisms, a culture medium generally used in the production of amino acids through fermentation is employed. That is, a culture medium containing nutrients capable of being assimilated by the microorganisms, such as a carbon source, a nitrogen source, inorganic salts and the like is used. Such culture media are well known in the art.

Examples of the carbon source include glucose, fructose, sucrose, molasses, and starch hydrolyzate. Examples of the nitrogen source include ammonia, ammonium sulfate, ammonium chloride, ammonium nitrate, ammonium phosphate, urea, organic acid ammonium salts, amines, other nitrogen compounds, yeast extract, peptone, soybean hydrolyzate, fermented strains and digested substances thereof. These (nitrogen and carbon sources) may be used either singly or in combination. Examples of the organic salts include potassium dihydrogen phosphate, manganese sulfate, iron sulfate, and magnesium sulfate. Mixtures may be used.

Other nutrient sources such as amino acids, vitamins, peptones, yeast extract, casamino acid and the like may be added to a culture medium if it is required for growth of strains and formation of L-leucine.

Incubation is conducted under aerobic conditions such as aerial stirring, shaking and the like at an incubation temperature of from 20° to 45° C., preferably from 26° to 40° C. The pH during the incubation is adjusted to from 5 to 10, preferably from 6 to 8 through addition of acid or alkali as required. The incubation time is between 10 to 170 hours, preferably between 16 and 72 hours. L-leucine is formed and accumulated in the thus-obtained culture solution. In the process of the present invention, the cells contained in the culture are further reacted with one or more saccharides and acetic acid or its salt, whereby L-leucine is further formed and accumulated. Examples of acetic acid salts are Na, Li, K, ammonium, etc. salts. Mixtures may be used. Examples of the saccharides with which the cells are reacted include glucose, fructose, sucrose, molasses, and starch hydrolyzate.

Invention methods in which the cells are reacted with saccharides and acetic acid or its salt include a method in which a culture containing the cells is used as such and saccharides and acetic acid or its salt are added thereto for reaction, and a method in which the cells are separated and recovered from the culture solution, and then added to an aqueous solution (reaction solution) containing saccharides and acetic acid or its salt for reaction.

In the method in which a culture containing the cells is used as such and saccharides and acetic acid or its salt are added thereto for reaction, the amount of saccharides (one or more) added is between 0.1 to 300 g/liter, preferably between 1 and 150 g/liter, including 10, 20, 30, 40, 50, 60, 70, 80, 90, 100, 110, 120, 130 and 140 and all values and subranges therebetween, and the amount of acetic acid or its salt is between 0.1 and 300 g/liter, preferably between 1 and 50 g/liter in terms of acetic acid including 5, 10, 15, 20, 25, 30, 35, 40 and 45 and all values and subranges therebetween. A weight ratio of acetic acid/saccharides is between 0.01 and 10, preferably between 0.1 and 3 including 0.5, 1, 2, 4, 5, 6, 7, 8 and 9 and all values and subranges therebetween.

In the method in which the cells are separated and recovered from the culture solution, and added to an aqueous solution (reaction solution) containing saccharides and acetic acid or its salt for reaction, a reaction solution containing the above-mentioned saccharides and acetic acid or its salt in the above concentrations as well as a nitrogen source, inorganic salts and other nutrients which the microorganisms can utilize is used as the reaction solution which is reacted with the separated cells. Amino acids required for growth of microorganisms may be removed in order not to cause proliferation of the cells in the reaction solution.

The amount of the saccharides in the reaction solution preferably is between 0.1 and 300 (see above) g/liter, more preferably between 5 and 150 g/liter, and the amount of acetic acid or its salt is between 0.1 and 300 g/liter (see above), more preferably between 0.5 and 50 g/liter in terms of acetic acid. A weight ratio of acetic acid/saccharides is between 0.01 and 10 (see above), more preferably between 0.05 and 3.

Examples of the nitrogen source include ammonia, ammonium sulfate, ammonium chloride, ammonium nitrate, ammonium phosphate, urea, organic acid ammonium salts, amines, other nitrogen compounds, yeast extract, peptone, soybean hydrolyzate, fermented strains and digested substances thereof. These may be used either singly or in combination.

Examples of the inorganic salts include potassium dihydrogen phosphate, manganese sulfate, iron sulfate and magnesium sulfate. Other nutrient sources such as amino acids, vitamins, peptone, yeast extract, casamino acid and the like may be added if it is required for formation of L-leucine.

When the incubated cells are reacted with saccharides and acetic acid or its salt to form L-leucine, the reaction is conducted under aerobic conditions such as aerial stirring, shaking and the like at a reaction temperature of from 20° to 45° C., preferably from 25° to 40° C. The pH during the reaction is adjusted to from 5 to 10, preferably from 6 to 8 through addition of acid or alkali as required. The reaction time is between 1 and 72 hours, preferably between 6 and 40 hours, including 10, 20 and 30 and all values and subranges therebetween.

After the completion of the reaction, L-leucine may be collected from the reaction solution by removing the precipitate such as the cells or the like from the reaction solution and then conducting concentration, salting-out, isoelectric precipitation or the like as required and may optionally be purified by art-accepted techniques, if desired.

EXAMPLES

The present invention will be illustrated more specifically by referring to the following non-limiting Examples.

The amounts of L-leucine and L-valine were determined by analyzing the supernatant of the reaction solution from which the cells were removed through centrifugation by means of an amino acid analyzer.

EXAMPLE 1

*Corynebacterium glutamicum* AJ3453 (FERM BP-5360) was grown in a reserved agar medium having a composition shown in Table 1.

TABLE 1

| Ingredients | Amount |
|---|---|
| glucose | 5 g/liter |
| NaCl | 5 g/liter |
| yeast extract | 10 g/liter |
| polypeptone | 10 g/liter |
| Dl-methionine | 0.1 g/liter |
| agar | 15 g/liter |
| pH 7.2 | |

Subsequently, one platinum loopful of the culture was inoculated in 20 ml of an L-leucine-productive medium having a composition shown in Table 2 which medium was charged in a 500-milliliter flask, and the culture was incubated at 31.5° C. for 40 hours while being shaken to obtain a culture containing cells. To this culture were added 2 g/liter of glucose and 4 g/liter of sodium acetate, and the mixture was reacted at 31.5° C. for 32 hours while being shaken.

TABLE 2

| Ingredients | Amount |
|---|---|
| glucose | 100 g/liter |
| ammonium sulfate | 45 g/liter |
| $KH_2PO_4$ | 1 g/liter |
| $MgSO_4.7H_2O$ | 1 g/liter |
| $FeSO_4.7H_2O$ | 0.01 g/liter |
| $MnSO_4.5H_2O$ | 0.01 g/liter |
| biotin | 100 g/liter |
| vitamin $B_1$ | 1000 g/liter |
| DL-methionine | 300 mg/liter |
| L-isoleucine | 100 mg/liter |
| soybean hydrolyzate (in terms of the total nitrogen | 150 mg/liter |
| calcium carbonate | 50 g/liter |
| pH 7.0 | |

The amounts of L-leucine and L-valine were determined when the reaction was started (when the incubation was completed) and when the reaction was completed. As a control, 2 g/liter of glucose alone was added to the culture, and the mixture was reacted in the abovementioned manner.

As a result, it was confirmed, as shown in Table 3, that when the reaction was conducted upon the addition of glucose alone, the amount of L-valine by-product was increased as L-leucine was formed and accumulated, and that when the reaction was conducted upon the addition of glucose and sodium acetate, L-leucine alone was formed and accumulated through the reaction, and a ratio of L-valine to the final product was decreased.

TABLE 3

|  | Addition of glucose and acetic acid | | Addition of glucose alone | |
|---|---|---|---|---|
|  | Amount of L-Leu accumulated (g/liter) | Amount of L-Val accumulated (g/liter) | Amount of L-Leu accumulated (g/liter) | Amount of L-Val accumulated (g/liter) |
| When the reaction was started | 18.3 | 1.9 | 18.6 | 1.8 |
| When the reaction was completed | 27.0 | 1.9 | 24.9 | 3.0 |

EXAMPLE 2

*Escherichia coli* AJ11478 (FERM BP-5361 was grown in a reserved agar medium having a composition shown in Table 4. Subsequently, one platinum loopful of the culture was inoculated in 20 ml of an L-leucine-productive medium having a composition shown in Table 5 which medium was charged in a 500-milliliter flask, and the culture was incubated at 37° C. for 24 hours while being shaken to obtain a culture containing cells. To this culture were added 2 g/liter of glucose and 4 g/liter of sodium acetate, and the mixture was reacted at 37° C. for 16 hours while being shaken. The amounts of L-leucine and L-valine were determined when the reaction was started (when the incubation was completed) and when the reaction was completed. As a control, 2 g/liter of glucose alone was added to the culture, and the mixture was reacted in the above-mentioned manner.

TABLE 4

| Ingredients | Amount |
|---|---|
| bactotrypton | 10 g/liter |
| yeast extract | 5 g/liter |
| NaCl | 5 g/liter |
| pH 7.2 |  |

TABLE 5

| Ingredients | Amount |
|---|---|
| glucose | 50 g/liter |
| ammonium sulfate | 25 g/liter |
| KH$_2$PO$_4$ | 2 g/liter |
| MgSO$_4$.7H$_2$O | 1 g/liter |
| yeast extract | 0.5 g/liter |
| FeSO$_4$.7H$_2$O | 0.01 g/liter |
| MnSO$_4$.5H$_2$O | 0.01 g/liter |
| calcium carbonate | 25 g/liter |
| vitamin B$_1$ | 300 µg/liter |
| pH 7.0 |  |

As a result, it was confirmed, as shown in Table 6, that when the reaction was conducted upon the addition of glucose alone, the amount of L-valine by-product was increased as L-leucine was formed and accumulated, and that when the reaction was conducted upon the addition of glucose and sodium acetate, L-leucine alone was formed and accumulated through the reaction, and a ratio of L-valine to the final product was decreased.

TABLE 6

|  | Addition of glucose and acetic acid | | Addition of glucose alone | |
|---|---|---|---|---|
|  | Amount of L-Leu accumulated (g/liter) | Amount of L-Val accumulated (g/liter) | Amount of L-Leu accumulated (g/liter) | Amount of L-Val accumulated (g/liter) |
| When the reaction was started | 1.2 | 0.12 | 1.26 | 0.13 |
| When the reaction was completed | 1.9 | 0.09 | 1.4 | 0.23 |

EXAMPLE 3

*Corynebacterium glutamicum* AJ3453 (FERM BP-5360) was incubated under the same conditions as in Example 1 for 48 hours, and the cells were recovered from the culture corresponding to one flask through centrifugation. The cells were washed with 0.2% KCl, and suspended in 75 ml of a reaction solution obtained by adding various amounts of sodium acetate to a composition shown in Table 7. The suspension was reacted for 16 hours while being shaken. After the completion of the reaction, the amounts of L-leucine and L-valine formed and accumulated in the reaction solution were determined. As a control, the reaction was conducted in the above-mentioned manner except that sodium acetate was not added.

TABLE 7

| Ingredients | Amount |
|---|---|
| glucose | 10 g/liter |
| KH$_2$PO$_4$ | 4.5 g/liter |
| Na$_2$HPO$_4$ | 23.9 g/liter |
| ammonium sulfate | 6 g/liter |
| MgSO$_4$.7H$_2$O | 0.5 g/liter |
| FeSO$_4$.7H$_2$O | 0.01 g/liter |
| MnSO$_4$.5H$_2$O | 0.01 g/liter |
| biotin | 50 µg/liter |
| vitamin B$_1$ | 300 µg/liter |
| pH 7.0 |  |

Consequently, as shown in Table 8, the addition of sodium acetate in the amount of from 2 to 32 g/liter decreased the ratio of L-valine accumulated to L-leucine accumulated and increased the amount of L-leucine accumulated as compared to the case of not adding sodium acetate.

TABLE 8

| Amount of sodium acetate added (g/liter) | Acetic acid/glucose ratio | Amount of L-Leu accumulated (g/liter) | Ratio of L-Val accumulated/L-Leu accumulated (%) |
|---|---|---|---|
| 0 | 0 | 3.2 | 7.0 |
| 2 | 0.14 | 3.7 | 5.8 |
| 4 | 0.3 | 4.4 | 4.0 |
| 8 | 0.6 | 4.6 | 1.9 |

TABLE 8-continued

| Amount of sodium acetate added (g/liter) | Acetic acid/glucose ratio | Amount of L-Leu accumulated (g/liter) | Ratio of L-Val accumulated/L-Leu accumulated (%) |
| --- | --- | --- | --- |
| 16 | 1.2 | 5.1 | 1.3 |
| 32 | 2.3 | 4.9 | 1.5 |

As described and shown above, the process of the present invention improves the amount of L-leucine accumulated and decreases formation of amino acids as by-products in the production of L-leucine using microorganisms, whereby L-leucine can be produced industrially at low costs.

Obviously, numerous modifications and variations of the present invention are possible in light of the above teachings. It is therefore to be understood that within the scope of the appended claims, the invention may be practiced otherwise than as specifically described herein.

This application is based on Japanese Application 072937/1995 filed Mar. 30, 1995, incorporated herein by reference.

What is claimed as new and is desired to be secured by letters patent of the United States is:

1. A process for producing L-leucine, comprising the steps of:
    culturing an L-leucine producing microorganism belonging to the genus Corynebacterium, Escherichia, Brevibacterium or Microbacterium in a first culture medium;
    incubating said microorganism in a second culture medium comprising 0.1 to 300 g/L of one or more saccharides and 0.1 to 300 g/L of acetic acid or a salt thereof calculated in terms of acetic acid to produce L-leucine in said second culture medium, wherein the weight ratio of acetic acid or a salt thereof to saccharides is between 0.01 and 10; and
    isolating L-leucine from said second culture medium.

2. The process as claimed in claim 1, wherein said second culture medium comprises 1 to 150 g/L of one or more saccharides and 1 to 50 g/L of acetic acid or a salt thereof.

3. The process as claimed in claim 2, wherein the weight ratio of acetic acid or a salt thereof to saccharides is between 0.05 and 3.

4. The process as claimed in claim 1, wherein the weight ratio of acetic acid or a salt thereof to saccharides is between 0.05 and 3 in said second culture medium.

5. The process as claimed in claim 1, wherein the weight ratio of acetic acid or a salt thereof to saccharides is between 0.1 and 3 in said second culture medium.

6. The process as claimed in claim 1, wherein said first culture medium comprises one or more saccharides as the main carbon source.

7. The process as claimed in claim 1, wherein said microorganism belongs to the genus Corynebacterium.

8. The process as claimed in claim 1, wherein said microorganism is *Corynebacterium glutamicum*, *Corynebacterium acetoacidophilum*, *Corynebacterium acetoglutamicum*, *Corynebacterium lilium* or *Corynebacterium melassecola*.

9. The process as claimed in claim 1, wherein said microorganism is *Corynebacterium glutamicum*.

10. The process as claimed in claim 1, wherein said microorganism belongs to the genus Escherichia.

11. The process as claimed in claim 1, wherein said microorganism is *Escherichia coli*.

12. The process as claimed in claim 1, wherein said microorganism belongs to the genus Brevibacterium.

13. The process as claimed in claim 1, wherein said microorganism is *Brevibacterium lactofermentum*, *Brevibacterium saccharolyticum* or *Brevibacterium flavum*.

14. The process as claimed in claim 1, wherein said microorganism is *Brevibacterium lactofermentum*.

15. The process as claimed in claim 1, wherein said microorganism belongs to the genus Microbacterium.

16. The process as claimed in claim 1, wherein said microorganism is *Microbacterium ammoniaphilum*.

17. The process as claimed in claim 1, wherein said microorganism belongs to the genus Corynebacterium or Escherichia, or is *Brevibacterium lactofermentum* or *Brevibacterium flavum*.

18. The process as claimed in claim 1, wherein said microorganism is *Corynebacterium glutamicum* AJ3453, *Escherichia coli* AJ11478 or *Brevibacterium lactofermentum* AJ3718.

19. The process as claimed in claim 1, wherein said microorganism is *Corynebacterium glutamicum* AJ3453 or *Escherichia coli* AJ11478.

20. The process as claimed in claim 1, wherein the culturing step is conducted under aerobic conditions for from 10 to 170 hours at a temperature of from 20° to 45° C. at a pH of from 5 to 10.

21. The process as claimed in claim 1, wherein the incubating step is conducted under aerobic conditions for from 1 to 72 hours at a temperature of from 20° to 45° C. at a pH of from 5 to 10.

22. The process as claimed in claim 1, further comprising after the culturing step, adding said one or more saccharides and said acetic acid or a salt thereof to said first culture medium to produce said second culture medium.

23. The process as claimed in claim 1, further comprising after the culturing step, separating and recovering said microorganism from said first culture medium and then adding said microorganism to said second culture medium.

* * * * *